United States Patent
Woods et al.

(10) Patent No.: US 10,632,247 B1
(45) Date of Patent: Apr. 28, 2020

(54) APPARATUS, SYSTEMS, AND METHODS FOR DELIVERING AGENTS INTO A PATIENT'S BODY

(71) Applicant: CLPH, LLC, Palo Alto, CA (US)

(72) Inventors: Christopher E. Woods, Palo Alto, CA (US); Christian S. Eversull, Palo Alto, CA (US); Stephen A. Leeflang, Sunnyvale, CA (US)

(*) Notice: Subject to any disclaimer, the term of this patent is extended or adjusted under 35 U.S.C. 154(b) by 472 days.

(21) Appl. No.: 14/604,671

(22) Filed: Jan. 23, 2015

Related U.S. Application Data

(60) Provisional application No. 61/930,844, filed on Jan. 23, 2014.

(51) Int. Cl.
| | |
|---|---|
| *A61B 5/00* | (2006.01) |
| *A61M 5/00* | (2006.01) |
| *A61B 5/0402* | (2006.01) |
| *A61M 25/10* | (2013.01) |
| *A61B 18/24* | (2006.01) |
| *A61B 5/0215* | (2006.01) |
| *A61B 18/00* | (2006.01) |

(52) U.S. Cl.
CPC ........... *A61M 5/007* (2013.01); *A61B 5/0044* (2013.01); *A61B 5/0071* (2013.01); *A61B 5/0084* (2013.01); *A61B 5/0215* (2013.01); *A61B 5/0402* (2013.01); *A61B 18/24* (2013.01); *A61M 25/10* (2013.01); *A61B 2018/00386* (2013.01); *A61B 2018/00577* (2013.01); *A61B 2018/00648* (2013.01); *A61B 2018/00839* (2013.01); *A61B 2018/00982* (2013.01); *A61M 2210/125* (2013.01)

(58) Field of Classification Search
CPC ...... A61B 18/1492; A61B 2017/00057; A61B 2090/065; A61B 5/0084; A61B 5/1107; A61B 5/6885; A61M 2025/105; A61M 2025/1052; A61M 25/10
See application file for complete search history.

(56) References Cited

U.S. PATENT DOCUMENTS

| | | | | |
|---|---|---|---|---|
| 4,909,258 | A * | 3/1990 | Kuntz | A61B 6/481 600/435 |
| 5,678,550 | A * | 10/1997 | Bassen | A61B 5/0084 600/342 |
| 7,213,601 | B2 * | 5/2007 | Stevens | A61B 17/00234 128/898 |
| 2008/0058591 | A1 * | 3/2008 | Saadat | A61B 1/0008 600/109 |
| 2008/0081990 | A1 * | 4/2008 | Berenfeld | A61B 1/042 600/420 |

(Continued)

*Primary Examiner* — Joel Lamprecht
(74) *Attorney, Agent, or Firm* — William A. English; Vista IP Law Group LLP

(57) ABSTRACT

Systems and methods are provided for imaging cardiac tissue using fluorescent dyes delivered into tissue. A distal end of an imaging device may be introduced into a chamber of the heart, and fluorescent dye may be delivered into one or more body lumens in the heart such that the dye is absorbed by cardiac tissue adjacent the chamber. Images of the cardiac tissue adjacent the chamber may be acquired using the imaging device, the dye enhancing identifying cardiac electrical activity within the cardiac tissue. Optionally, based on the identified cardiac electrical activity, tissue within the heart may be ablated or otherwise treated.

22 Claims, 2 Drawing Sheets

(56) References Cited

U.S. PATENT DOCUMENTS

2010/0160720 A1\* 6/2010 Eby ................. A61B 5/0084
600/37
2016/0038027 A1\* 2/2016 Brzozowski ......... A61B 5/0059
600/431

\* cited by examiner

APPARATUS, SYSTEMS, AND METHODS FOR DELIVERING AGENTS INTO A PATIENT'S BODY

RELATED APPLICATION DATA

This application claims benefit of provisional application Ser. No. 61/930,844, filed Jan. 23, 2014, the entire disclosure of which is expressly incorporated by reference herein.

STATEMENT REGARDING FEDERALLY SPONSORED RESEARCH AND DEVELOPMENT

The U.S. Government may have a paid-up license in this invention and the right in limited circumstances to require the patent owner to license others on reasonable terms as provided for by the terms of Grant No. 1R43HL116017-01A1 awarded by the National Institutes of Health of the Department of U.S. Health and Human Services.

FIELD OF THE INVENTION

The present invention relates generally to apparatus, systems, and methods for delivering agents into a patient's body, and more particularly to apparatus, systems, and methods for delivering optically active agents into a patient's tissues to facilitate imaging the tissues.

BACKGROUND

Optically active agents have historically been used in the research setting for monitoring electrophysiology. As one example, voltage-sensitive and calcium-sensitive fluorescent dyes can be used to monitor cardiac electrical activity and associated contractile function. However, these techniques have not been applied in a clinical setting, nor usefully in living large animal models.

Further, optical imaging of voltage and calcium dyes requires, among other things, light sensors (e.g., CCD, CMOS, etc.) capable of measuring small intensity fluctuations on a large baseline signal at a high frame-rate, adequate illumination in one or more wavelength ranges, and/or filtering of excitation and/or illumination light.

A wide range of such dyes exist for use in research and are widely used in explanted hearts (e.g., Langendorff preparations) and in small animal models. These include conventional dyes such as Di-4-ANEPPS as well as newer generation ratiometric dyes and near IR emission dyes. Relatedly, techniques are even emerging to genetically encode proteins with similar optical activity.

Dyes of this type are typically lipophilic (to varying degrees) and are rapidly taken up into the cell wall as they pass through a capillary bed. Experimentally, loading of these dyes is most often performed in a substantially blood free environment, e.g., where tissue blood perfusion is either briefly, or in a sustained manner replaced by an alternative fluid that is largely devoid of cells. A variety of such preparations exist for Langendorff models, particularly those deriving from small mammals. In a live small animal model, blood may be temporarily excluded from the vessels and/or tissue, for example, by infusion of large volumes of saline. Dye may be put into solution with or without amphipathic agents (e.g., DMSO, PEG, etc.) and loading may take place in this environment.

When blood is present, lipophilic dyes may be rapidly consumed by red blood cells, white blood cells, platelets, etc. before they are able to reach the capillary bed and be absorbed by cardiomyocytes, etc. Additionally, when flow rates are high, dye may be rapidly diluted, further decreasing the effective concentration that is delivered to the capillary bed.

Due to the complexity of loading dyes in-vivo and the optical systems required for imaging, minimally invasive techniques and tools for in-vivo optical mapping have not been developed.

Therefore, improved methods for loading dyes in blood perfused tissue and imaging tissues loaded with such dyes would be useful.

SUMMARY

The present invention is directed to apparatus, systems, and methods for delivering agents into a patient's body. More particularly, the present invention is directed to apparatus, systems, and methods for delivering optically active agents, e.g., lipophilic and/or fluorescent dyes, into a patient's tissues to facilitate imaging the tissues.

In accordance with one embodiment, a method is provided for imaging tissue during a medical procedure that includes introducing a distal end of an imaging device into a chamber of the heart; delivering fluorescent dye into one or more body lumens in the heart such that the dye is absorbed by cardiac tissue adjacent the chamber; and acquiring images of the cardiac tissue adjacent the chamber using the imaging device, the dye enhancing imaging and/or identifying cardiac electrical activity within the cardiac tissue. A variety of methods may be used for delivering the dye, e.g., to preferentially deliver the dye into the capillaries of the heart rather than being absorbed by blood flowing through the heart.

For example, in a first method, a relatively high concentration of dye may be prepared, e.g., dye supersaturated in an appropriate carrier prior to infusion. A highly concentrated infusion solution may be rapidly injected and exposed to/mixed with a smaller volume of blood prior to reaching the capillary bed and generally retain a sufficiently high concentration of dye to be effectively taken up by tissue.

Another method may involve removing a volume of blood, adding a large amount of dye, e.g., to exceed the uptake capacity of that volume, leaving some dye free, and then re-injecting the blood with dye.

Yet another method may involve minimizing dye mixing with blood so that dye and its carrier may reach the capillary bed with minimal exposure to blood cells. For example, dye may be infused from a catheter or other apparatus that generally creates a laminar flow or otherwise minimizes mixing when infused into the circulation. For example, such a catheter may be used to engage a coronary artery and infuse the dye with carrier so that dye transits through the large vessels with minimal mixing with blood.

In an alternative embodiment, a catheter or other apparatus may be constructed to infuse a fluid including dye, accompanied by a protective fluid. For example, a dye solution may be injected through a central lumen. A generally annular lumen may surround the central lumen, and a second fluid, for example, saline, plasma, carbon dioxide ($CO_2$), and the like, may be infused around the central stream of dye containing fluid to further decrease the degree of mixing that occur in larger vessels.

In a further alternative, a dye carrier may be used that is generally less miscible with blood, for example, dimethyl sulfoxide (DMSO), iodinated contrast, hydrogel such as polyethylene glycol (PEG), and the like. These, or other appropriate fluids, may resist mixing during transit through the large vessels, allowing dye solution to reach the capillaries exposed to fewer blood cells, and/or with a higher concentration of available dye.

In yet a further embodiment, the dye and/or its carrier may be generally adapted to reduce the absorption of dye by blood cells. For example, the dye itself, and/or in combination with the carrier, and/or other additives to the mixture may form a protective configuration. As one example, this may be similar to a micelle. As another example, proteins or other molecules may be used to temporarily reduce absorption/stabilize the dye. The protective configuration may render the dye relatively less rapidly absorbed into cell membranes, e.g., those of blood cells. The protective nature of the configuration may be generally transient. For example, the size of the protective configuration may be such that it breaks down when passing from the larger vessels into the capillaries. Alternatively, the protective configuration may be time dependent, e.g. designed to degrade in the time of transit to the capillaries.

In a further embodiment, the dye and/or its delivery method may generally comprise a slower rate of absorption such that dye is not readily absorbed by cells in the short transit time through large vessels, but is generally absorbed in the slower transit time through the capillaries.

In a further embodiment, blood flow may be temporarily excluded. For example, a balloon-tipped sheath, or simply an appropriately sized (e.g., tight fitting) sheath may be used to engage a coronary artery, temporarily exclude blood flow, and infuse dye. Moreover, a sufficiently large volume injection into a coronary artery and/or aorta may effectively temporarily exclude blood flow. A dye carrier with some oxygen carrying capacity may be included, e.g., to minimize ischemia potentially caused by excluding blood.

In an alternative embodiment, an occlusion device (e.g., a balloon) may be placed in the aorta (e.g., in the ascending aorta) and a dye or other agent may be infused into the isolated space distal to and against a substantially closed aortic valve. Using such an approach, both coronary vessels may be perfused contemporaneously.

In yet an alternative embodiment, dye may be introduced into the heart retrograde via the coronary sinus. For example, the coronary sinus may be temporarily occluded and dye may be infused and remain resident within the veins and/or capillaries for a duration sufficient to achieve absorption into the tissue. In this embodiment, the delivery device may be adapted to engage the coronary sinus and/or its tributary vessels and may further include an occlusion member (e.g., a balloon and the like) to enable infusion of fluid into the coronary veins at increased pressure. In this way, dye may be perfused retrograde into the coronary capillary bed in order to diffuse into the cardiac cells. Further, various methods may be used to decrease the upstream pressure against which retrograde perfusion must occur.

Optionally, in combination with alternatively to any of these methods, cardioplegia may be performed in order to stop forward flow and/or decrease temperature and metabolic activity of the heart to facilitate dye loading. Alternatively, the heart may be at least temporarily rapidly paced in order to decrease contractility and mean arterial pressure. Such strategies may be employed in conjunction with an antegrade (e.g., via the coronary arteries) or retrograde (e.g. via the coronary sinus) approach.

Further, in both antegrade and retrograde approaches, the vascular territory may be sub-selected or isolated in order to selectively apply dye to the region of most interest. For example, if investigating a ventricular arrhythmia originating from the left ventricular (LV) anterior wall, the left anterior descending artery (LAD) may be selectively injected with dye.

Optionally, in addition, monitoring may be performed either in the coronary veins or coronary arteries, e.g., to detect the presence and/or measure the concentration of dye introduced. For example, a detection catheter may be placed in the coronary sinus while dye is introduced into a coronary artery. Dye presence and/or characteristics in the coronary sinus may be monitored to ascertain achievement of adequate or optimal loading. For example, an optical detection device may be placed in the coronary sinus capable of detecting dye and/or measuring concentration.

In another embodiment, dye may be applied directly to cardiac tissue in order to achieve loading. For example, a catheter apparatus may be adapted with one or more isolation elements adapted to create a fluid channel to substantially isolate blood from a selected area of cardiac tissue. For example, a catheter may be adapted with a funnel-like expandable element which may be collapsible. When positioned at a desired location within the heart, the element may be expanded and its distal end may be positioned against a wall of the heart, e.g., substantially seal against the wall of the heart and/or provide a space at least partially isolated from the chamber. For example, such an apparatus may be introduced either endocardially or epicardially in order to isolate a portion of the heart wall. Once isolation is achieved, dye may be introduced into the isolated area and held in place for a predetermined time to allow for loading into the tissue. Excess dye may then be removed and/or the area may be rinsed (e.g., with saline, etc.) to eliminate excess dye. This procedure may be performed one or more time to apply dye to the desired area of the heart.

Further alternatively, dye may be introduced with or without provision for site selectivity into the pericardial space. In this case, blood is not present and therefore the dye would not be subject to absorption and/or dilution caused by blood. Dye may be applied to tissue epicardially in a localized fashion, for example, as described above, or in a generalized fashion. For example, a dye solution may be introduced into the pericardial space and allowed to reside there for a predetermined amount of time to provide for absorption into tissue. Excess dye may then be removed and/or a wash/rinse performed (e.g., with saline, and the like) to remove excess dye.

Optionally, in any of these embodiments, cardiac tissue may be treated, e.g., based at least in part on the images acquired using the imaging device. For example, laser energy may be delivered via the imaging device, e.g., using a fiberoptic bundle also used for acquiring the images, to ablate desired regions of the cardiac tissue. In another embodiment, light may be delivered via the imaging device to ablate and/or otherwise damage target tissue. For example, a high-intensity LED or laser may be used to deliver light at a peak-absorbed spectrum of the dye absorbed by the cardiac tissue. As a result, the dye may generate free radicals to ablate and/or otherwise damage tissue within which the dye is absorbed.

In addition or alternatively, in any of the embodiments herein, the acquired images may be used to identify and/or treat channelopathies. For example, because scar tissue has little or no blood flow, such tissue may not absorb the dye and, therefore, appear as dark regions in acquired images. However, if channels of electrical conductivity remain, they may be highlighted by the dye as bright regions in the images, and so may be identified for treatment, e.g., ablation using the imaging device or another device.

In accordance with another embodiment, a pacemaker system may be implanted within a patient's body that includes a fiberoptic lead positioned within a desired location within the patient's heart. Fluorescent dye (genetically engineered or otherwise) may be placed within tissue of the heart, which may be monitored to at least partially control the pacemaker. For example, rather than requiring an imaging fiberoptic bundle, a single fiber may be coupled to a photo diode, which may detect a threshold light intensity based on the dye to at least partially determine parameters for operating the pacemaker.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which.

DETAILED DESCRIPTION OF THE EXEMPLARY EMBODIMENTS

Figure 1:
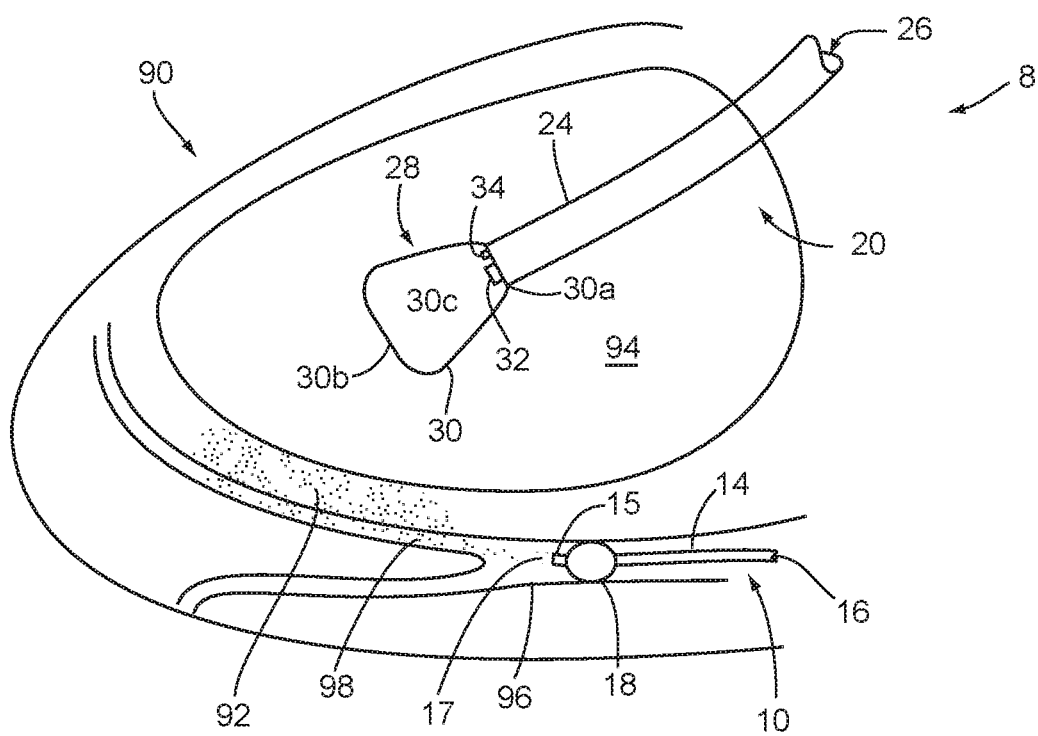
FIG. 1 is a cross-sectional view of a portion of a heart showing a method for delivering dyes into cardiac tissue to enhance imaging of the tissue.

Turning to the drawings, FIG. 1 shows an exemplary embodiment of a system 8 for performing a medical procedure within a patient's body, e.g., for imaging within the patient's heart 90 and/or injecting one or more agents into one or more tissues or lumens, e.g., into the wall 92 of a patient's heart 90. Generally, as shown, the system 8 includes a delivery catheter or sheath 10, e.g., for delivering one or more dyes or other agents into cardiac tissue of the heart 90, and an imaging catheter 20, e.g., for imaging cardiac electrical activity within the heart 90.

The sheath 10 may be an elongate tubular member including a proximal end (not shown), a distal end 14 sized for insertion into a patient's body, and one or more lumens 16 extending between the proximal and distal ends 14. For example, the sheath 10 may include an infusion lumen 16 communicating from a port on a handle on the proximal end (not shown) and one or more outlets 17 in a distal tip 15 of the sheath 10. In an exemplary embodiment, a source of fluorescent dye, e.g., a voltage-sensitive or calcium sensitive dye, may be coupled to the port on the proximal end, e.g., a syringe, pump, and the like (not shown), for delivering the dye into the patient's heart 90, e.g., for preferential absorption by the capillaries within the wall 92 of the heart 90, as described further elsewhere herein.

Optionally, as shown, the sheath 10 may also include a balloon or other expandable member 18 on the distal end 14, e.g., offset proximally from the distal tip 15, that may be selectively expanded to at least partially obstruct flow through a body lumen within which the distal end 14 is introduced. In addition or alternatively, the distal tip 15 may be rounded and/or otherwise substantially atraumatic, e.g., to facilitate advancement into blood vessels within the heart 90, such coronary artery 96 shown in FIG. 1.

Figure 2:
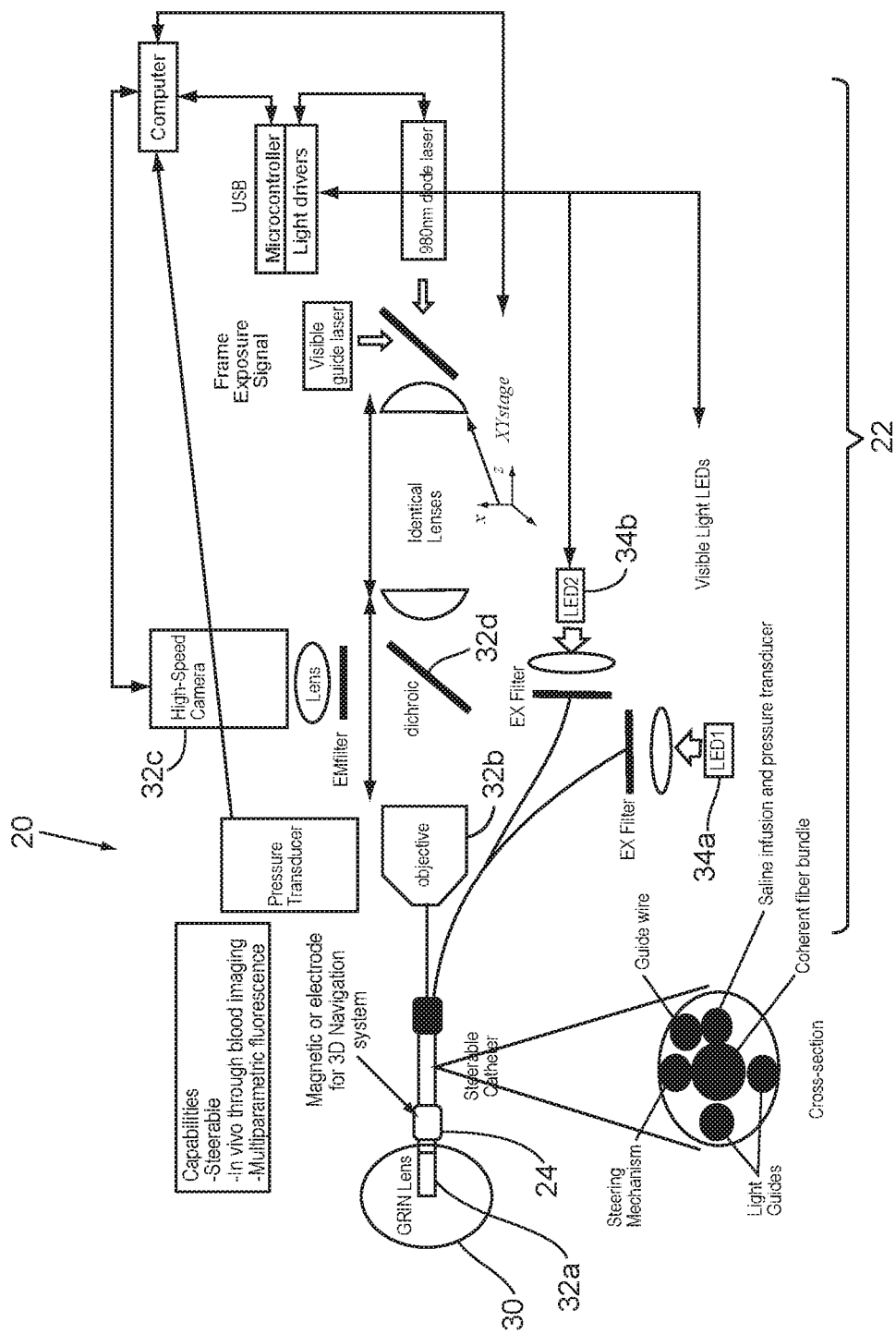
FIG. 2 is a schematic showing an exemplary embodiment of an imaging catheter that may be used in the systems and methods described herein.

With continued reference to FIG. 1 and additional reference to FIG. 2, the imaging catheter 20 is also a tubular member including a proximal end (not shown in FIG. 1; shown schematically in FIG. 2), a distal end 24, one or more lumens, e.g., inflation lumen 26, extending between the proximal and distal ends 22, 24, and an imaging assembly 28 on the distal end 24 for imaging within the patient's heart 90. Optionally, the catheter 20 may include one or more steering elements (not shown), e.g., for bending and/or otherwise directing the distal end 24 when introduced into a patient's body from the proximal end 22 outside the body. An exemplary embodiment of an imaging catheter 20 is shown in FIG. 2 and described further elsewhere herein. Additional embodiments of imaging catheters that may be used in the systems and methods herein are described in U.S. Pat. Nos. 6,979,290 and 8,050,746, and in co-pending U.S. application Ser. No. 14/542,545, the entire disclosures of which are expressly incorporated by reference herein.

Generally, as shown in FIG. 1, the imaging assembly 28 includes a balloon 30, an imaging element 32, and one or more light sources 34 mounted on the distal end 24, e.g., for imaging distally beyond the distal end 24 along a longitudinal axis of the imaging catheter 20. The balloon 30 may include a proximal end 30a attached to the distal end 24 of the catheter 20 and a distal surface 30b for placement against the wall 92 of the heart 90. Optionally, the balloon 30 may include a tubular extension or other passage therethrough and communicating with an accessory lumen in the catheter 20 (not shown), e.g., similar to those disclosed in the references incorporated by reference herein.

Alternatively, the balloon 30 may be omitted and the imaging catheter 20 may be configured to image through blood or other fluid. For example, the one or more light sources 34 may transmit light in the near-infrared range that may penetrate through blood and the imaging assembly 32 may acquire images reflected from the tissue and/or emitted by the tissue (e.g., after filtering reflected light to acquire the fluorescence light from the tissue) through the blood. In a further alternative, a controller may alter the imaging assembly 32 to alternate acquisition of reflected light and fluorescent emitted light images (in this or any other embodiment herein).

Returning to FIG. 1, the balloon 30 may be expandable from a contracted or delivery condition (not shown) to an enlarged condition when fluid is introduced into an interior 30c of the balloon 30, e.g., via the inflation lumen 26 within the catheter 20. Optionally, the balloon 30 may be shaped such that, in the enlarged condition, the balloon 30 may define a substantially flat distal surface 30b, which may facilitate imaging tissue structures beyond the balloon 30 using the imaging element 32.

In an exemplary embodiment, the balloon 30 may be formed from compliant and/or elastic materials, e.g., elastomeric materials such as silicone, latex, isoprene, and chronoprene. The compliance of the balloon 30 may facilitate clearing fluid between the distal surface 30b. Alternatively, the balloon 30 may be formed from substantially noncompliant material, e.g., polytetrafluoroethylene (PTFE), expanded polytetrafluoroethylene (EPTFE), fluorinated ethylenepropylene (FEP), polyethylene teraphathalate (PET), urethane, olefins, and polyethylene (PE), such that the balloon 30 expands to a predetermined shape when fully inflated to the enlarged configuration. The material may be sufficiently flexible and/or elastic such that the distal surface 30b may conform substantially to the shape of contacted tissue structures, which may displace blood or other fluid from between the distal surface 30b and the contacted tissue to facilitate imaging through the balloon 30.

The imaging element 32 may include one or more cameras or other elements configured to acquire images through the balloon 30 beyond the distal end 24 of the catheter 20. In an exemplary embodiment, the imaging element 32 may be a fiberoptic bundle that extends between the proximal and distal ends 24 of the catheter 20 and includes a plurality of fibers for capturing images. As shown in FIG. 2, the fiber bundle may terminate at the distal end 24 of the catheter at a lens 32a, e.g., a GRIN, conventional, or other lens, that may focus images and at the proximal end 22 at an objective lens 32b that may be optically coupled to a camera 32c, e.g., a CCD or CMOS device. Alternatively, the imaging element 32 may include one or more cameras, e.g., CCD or CMOS devices, mounted on the distal end 24, e.g., within the interior 30c of the balloon 30, and one or more cables or wires may extend from the distal end 24 to the proximal 22 for transmitting signals corresponding to the images.

Similarly, the light source(s) 34 may include one or more coherent fiber bundle and/or other fiber optic elements extending between the proximal and distal ends 22, 24 and coupled to one or more light sources at the proximal end 22. Alternatively, the light source(s) 34 may be one or more LEDs or other light sources mounted on the distal end 24, e.g., within the interior 30c of the balloon 30. In a further alternative embodiment, the imaging element 32 and light source(s) 34 may be provided as a single fiber bundle that extends between the proximal and distal ends 24 of the catheter 20 for both emitting light and capturing images.

In any case, emitted and/or detected light may be filtered, e.g., using narrow, long, and/or short band pass filters to optimize excitation of fluorescent dyes and/or detection of fluorescence signals produced.

As shown in FIG. 2, one or more features may be provided at the proximal end 22, e.g., within a handle of the catheter 20 or within a controller (not shown) coupled to the proximal end 22, for generating light and capturing and/or processing images. For example, as shown, two lights sources 34a, 34b may be provided that include two light emitting diodes LED1 and LED2 optically coupled to the fiber bundle, e.g., using one or more lenses, filters, and/or dichroic mirrors (not shown), etc. A controller may be coupled to the light sources 34a, 34b for selectively, e.g., alternately, activating LED1 and LED2, as described elsewhere herein. In exemplary embodiments, the LEDs may be configured to emit light at desired frequencies, e.g., generating visible light, for example white light or red light, and/or for generating infrared light, e.g., near-visible infrared light which may transmit through blood.

Also as shown in FIG. 2, a high speed camera 32c may be optically coupled to the fiber bundle, e.g., using one or more mirrors, filters, etc., for capturing images. Optionally, as shown, a dichroic mirror 32d and/or other optical elements may be provided at the proximal end 22, e.g., for allowing the fiberoptic bundle to be used for additional functions. For example, multiple cameras may be used, e.g. for simultaneous imaging of fluorescence activity and conventional visible light imaging of organ morphology. As a further example, as described elsewhere herein, a laser or other device may be coupled to the proximal end 22 that may be used to deliver energy via the fiberoptic bundle into the patient's body.

Returning to FIG. 1, during use, the system 8 may be used to deliver one or more agents, e.g., fluorescent dye, into tissue within a patient's heart 90, acquire images, and, optionally, perform one or more procedures within the heart 90. First, the delivery sheath 10 and imaging catheter 20 may be introduced into the patient's body and positioned at desired locations (in any desired order). For example, both may be introduced from a percutaneous entry site into the patient's vasculature, e.g., over a guidewire and/or via a guide sheath (not shown), and advanced into desired locations within the patient's heart 90.

As shown, the distal end 14 of the sheath 10 has been introduced into a coronary artery 96, e.g., via the aorta (not shown) and positioned upstream from a target region of cardiac tissue 92. Optionally, as shown, a balloon 18 on the distal end 14 may be inflated to substantially seal the artery 96 and temporarily stop blood flow downstream of the artery 96. Fluorescent dye 98 (and/or other agents) may then be infused into the artery 96 from the outlet 17 such that the dye 98 flows towards and is absorbed by the cardiac tissue 92. With blood flow discontinued, the dye 98 may be preferentially taken up by the capillary beds from the artery 96 into the cardiac tissue 92.

Various methods (not shown) may be used to monitor dye loading and/or ensure patient safety during loading. For example, the sheath 10 may include a pressure sensor, and/or a pressure sensor may be attached to and/or introduced through or alongside of the sheath 10 into the coronary artery 96. Coronary pressure may be measured directly or estimated during dye loading, e.g., to ensure that pressure does not exceed a predetermined level and/or to titrate loading rate to intra-vessel pressure. Further, various physiologic parameters may be measured and dye loading titrated thereto. For example, the EKG of the patient may be monitored for ST segment changes and/or other signs of acute ischemia and dye loading terminated, paused, and/or rate reduced to resolve such signs of ischemia. Alternatively, the sheath 10 may be introduced into other body lumens within the patient's body instead of the coronary artery 96 shown in FIG. 1. For example, the sheath 10 may be introduced into the coronary sinus (not shown) of the heart 90 and used to deliver the dye 98 retrograde into the cardiac tissue 92. Optionally, the balloon 18 may be expanded within the coronary sinus (or within coronary venous vessels) to substantially seal the vessels and reduce blood flow therethrough, which may enhance delivery of the dye 98 into the desired cardiac tissues.

In addition to or instead of using the balloon 18, as described elsewhere herein, other methods may be used to deliver the dye 98 into the cardiac tissue 92. For example, in an alternative embodiment, the distal end 14 of the sheath 10 may be sized to at least partially obstruct flow within the artery 92 such that merely inserting the distal end 14 into the artery 92 may reduce blood flow to ensure the dye 98 is absorbed into the cardiac tissue 92 rather than being absorbed and carried away by blood.

Optionally, the dye 98 may be delivered at a relatively high concentration to ensure sufficient dye 98 is absorbed into the cardiac tissue 92 and/or the dye 98 may include one or more carriers or formulations that enhance preferential absorption by the capillaries within the cardiac tissue 92 rather than by blood in the artery 96. For example, a dye carrier may be used that is generally less miscible with blood, for example, dimethyl sulfoxide (DMSO), iodinated contrast, hydrogel such as polyethylene glycol (PEG), and the like. These, or other appropriate fluids, may resist mixing during transit through the large vessels, allowing dye solution to reach the capillaries exposed to fewer blood cells, and/or with a higher concentration of available dye.

In yet a further embodiment, the dye 98 alone or in combination with one or more carriers and/or other additives may form a protective configuration, similar to a micelle. As another example, proteins or other molecules may be used to temporarily reduce absorption/stabilize the dye. The protective configuration may render the dye relatively less rapidly absorbed into cell membranes, e.g., those of blood cells. The protective nature of the configuration may be generally transient. For example, the size of the protective configuration may be such that it breaks down when passing from the larger vessels into the capillaries. Alternatively, the protective configuration may be time dependent, e.g. designed to degrade in the time of transit to the capillaries.

In another embodiment, the sheath 10 may be configured to enhance absorption by the capillaries of the cardiac tissue 92. For example, the sheath 10 may include multiple infusion lumens and concentric outlets communicating with the respective lumens (not shown). In this example, the dye 98 may be infused through a central outlet from a first infusion lumen, and a protective fluid may be delivered via one or more outer outlets, e.g., an annular outlet (not shown), surrounding the central outlet. The outer outlet(s) may communicate with a second infusion lumen coupled to a source of protective fluid at the proximal end of the sheath 10, such as saline, plasma, carbon dioxide (CO2), and the like (also not shown). The protective fluid may be delivered simultaneously with the dye 98, thereby infusing the fluid around the dye 98 to at least partially contain the dye 98 and reduce mixing with blood within the artery 96 before the dye 98 has a chance to be absorbed by the capillaries of the cardiac tissue 92.

Returning to FIG. 1, the distal end 24 of the imaging catheter 20 has been introduced into a chamber 94 of the heart 90, and the balloon 30 has then been expanded, as shown. The distal end 24 may then be manipulated, e.g., steered and/or advanced into contact with the wall of the heart 90, e.g., adjacent the cardiac tissue 92 within which dye 98 has been absorbed.

When the distal surface 30*b* of the balloon 30 is placed against the wall of the heart 90, blood or other fluid may be cleared away, and the cardiac tissue 92 may be imaged. For example, the light source(s) 34 may be used to deliver light at one or more desired wavelengths to activate the dye 98 and the imaging assembly 32 may then acquire images of the cardiac tissue 92. As described elsewhere herein, if the dye 98 is a voltage-activated fluorescent dye, the dye 98 may be activated by the light source(s) 34 and the electrical activity within the cardiac tissue 92, e.g., thereby providing both a visible image of the cardiac tissue 92 and the cardiac electrical activity therein.

The resulting images may be processed and/or analyzed, e.g., by a controller (not shown) coupled to the imaging catheter 20 and/or by the user to diagnose and/or treat the patient. For example, the resulting images may facilitate performing an electrophysiology procedure, e.g., to deliver energy to the cardiac tissue 92 to ablate and/or otherwise treat the tissue, e.g., caused by cardiac arrhythmia and/or other conditions.

With additional reference to FIG. 2, in an exemplary embodiment, a laser device (not shown) may be coupled to the proximal end 22 of the catheter 20 (e.g., via the dichroic mirror 32*d*) and used to deliver laser energy to ablate desired portions of the cardiac tissue 92. Alternatively, other forms of energy may be delivered via the catheter 20 and/or one or more devices delivered via the catheter 20, e.g., via an accessory lumen (not shown). Continued imaging of the cardiac tissue 92 during or following delivery of the energy may allow the user to immediately analyze the results to confirm that the cardiac electrical activity has been modified as desired. If needed, additional energy may be delivered and images acquired until the desired treatment is completed.

Once the desired procedure(s) is completed, the balloon 30 may be deflated and the catheter 20 removed from the heart 90 and the patient's body. The sheath 10 may also be removed from the artery 96 and the patient's body upon completing the procedure or once sufficient dye has been delivered into the cardiac tissue 92. Alternatively, the sheath 10 may be directed into other vessels within the heart 90 to image and/or treat other tissue regions, e.g., within the chamber 94 or within other locations in the heart 90, with the catheter 20 being manipulated as desired to image and/or treat other cardiac tissue.

Figure 3:
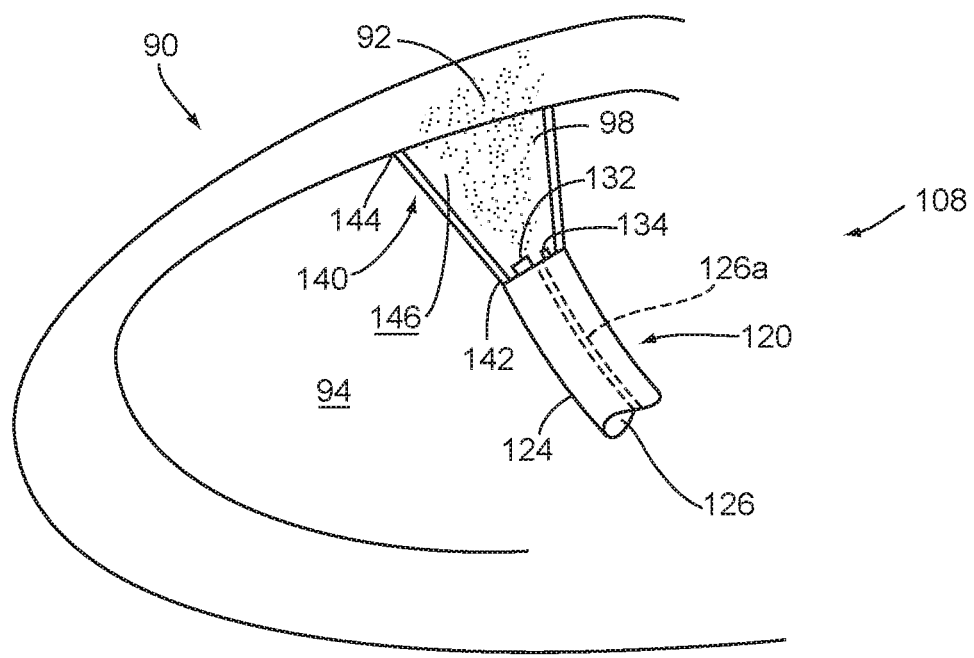
FIG. 3 is a cross-sectional view of a portion of a heart showing another method for delivering dyes into cardiac tissue and imaging the tissue.

Turning to FIG. 3, another exemplary embodiment of a system 108 is shown that may be introduced into a patient's heart to perform a diagnostic and/or therapeutic procedure that involves imaging cardiac tissue. Similar to other embodiments herein, the system 108 generally includes an imaging catheter 120 including a proximal end (not shown), a distal end 124 sized for introduction into the patient's body, and one or more lumens 126 extending therebetween. In addition, the catheter 120 includes an imaging assembly 132 and one or more light sources 134, which may also be similar to other embodiments herein.

Unlike the other embodiments, the catheter 120 includes an expandable hood 140 carried on the distal end 124, which includes a proximal end 142 attached to the catheter distal end 124 and an open distal end 144, e.g., having an annular or other desired shape. The hood 140 may be selectively directed between a contracted or delivery configuration (not shown) and an expanded configuration, shown in FIG. 3.

For example, the hood 140 may be constrained in the delivery configuration, e.g., by inserting the hood 140 into a delivery sheath, e.g., already introduced into the patient's body (not shown), and advancing the catheter 120 through the delivery sheath until the hood 140 is deployed from the delivery sheath, e.g., within the chamber 94, whereupon the hood 140 may resiliently expand to the expanded configuration. In an alternative embodiment, the hood 140 may include a frame or other expandable structure (not shown), which may be selectively actuated from the proximal end of the catheter 120 to direct the hood 140 between the contracted and expanded configurations. In another alternative, the hood 140 may include an annular balloon (not shown), e.g., defining the side wall of the hood 140 and/or the distal end 144 thereof, which may be inflated to cause the hood 140 to expand.

In the expanded configuration, the hood 140 may define a frusto-conical or other shape in which the hood 140 widens from the proximal end 142 to the distal end 144, thereby defining an inner space 146 therebetween. The hood 140 may be formed from a variety of materials, e.g., plastics, metals, or composite materials, that allow the hood 140 to be expanded and collapsed. In addition, the material may be sufficiently flexible to allow the distal end 144 to at least partially conform to the shape of tissue against which the hood 140 is pressed, e.g., while providing a substantially atraumatic contact area.

In addition, the catheter 120 includes an infusion lumen 126*a* extending from the proximal end to an outlet in the distal end 124, e.g., communicating with the space 146 within the hood 140. A source of one or more agents, e.g., fluorescent dye 98 may be coupled to the proximal end of the catheter 120, e.g., to a port on a handle (not shown), such that dye 98 may be infused into the space 146, as described further elsewhere herein.

During use, the catheter 120 may be introduced into a patient's body with the hood 140 in the contracted configuration and directed into the chamber 94 shown in FIG. 3, e.g., from a percutaneous entry site, through the patient's vasculature, and into the patient's heart 90. The hood 140 may be expanded and then the distal end 124 of the catheter 120 may be directed against the wall of the heart 90, e.g., by steering, advancing, and/or otherwise manipulating the distal end 124 from the proximal end of the catheter 120. The distal end 144 of the hood 140 may be pressed against the wall of the heart 90, e.g., to at least partially isolate the space 146 within the hood 140 from the rest of the chamber 94 of the heart 90.

For example, initially, a substantially clear fluid, e.g., saline, by delivered into the space 146 via the infusion lumen 126a to flush the space 146 of blood or other undesired fluids. This may be performed before placing the distal end 144 of the hood 140 against the wall of the heart 90 or while loosely holding the hood 140 against the wall such that the blood and flush the space 146 and escape into the chamber 94. Once sufficiently flushing has been accomplished, the hood 140 may be pressed further against the wall, if desired, to substantially seal the space 146 relative to the chamber 94.

Then, as shown in FIG. 3, dye 98 may be infused into the space 146 to enhance absorption of the dye 98 by cardiac tissue 92, similar to other embodiments herein. With the space 146 substantially clear of blood, the dye 98 may readily absorbed into the cardiac tissue 92.

The catheter 120 may then be used to acquire images of the cardiac tissue 92, e.g., obtaining both visible images of the tissue and cardiac electrical activity using the fluorescent dye 98, as described elsewhere herein with respect to other embodiments. The images may be used to analyze the patient's heart 90 and/or to treat the cardiac tissue 92, e.g., by delivering energy via the catheter 120 to ablate desired tissue, similar to other embodiments herein. Optionally, the hood 140 may be directed around the chamber 94 and pressed against multiple locations on the wall of the heart 90 to obtain images of larger areas of and/or treat the cardiac tissue 92. Once the desired procedure has been completed, the hood 140 may be collapsed, e.g., by advancing a delivery sheath (not shown) over the catheter 120 and hood 140 or otherwise collapsing the hood 140, and the catheter 120 may be removed.

In an exemplary embodiment, the systems and methods herein may be used to deliver voltage-sensitive dyes (VSDs) into cardiac tissues to enhance imaging cardiac electrical activity within the heart, e.g., to directly and/or substantially simultaneously visualize cardiac anatomy and ablation therapy. VSDs are membrane staining ampiphillic compounds with spectral properties that linearly report voltage changes in the membrane through changes in their emission intensity. The fast response times of VSDs permit a picture of voltage propagation (i.e., electrical activity) in the heart to be generated. Thus, using VSDs in combination with direct visualization catheters, it may be possible to substantially simultaneously measure the microscopic cellular cardiac action potential (AP) and macroscopic AP wave propagation over the tissue surface, while also visualizing anatomy.

By combining a direct visualization catheter with VSD measurements, optical electrophysiology offers the first truly electro-anatomic mapping simultaneously by allowing visualization of anatomy and physiology simultaneously or substantially simultaneously (e.g., in a rapidly alternating fashion). In addition, by using a camera to create these local and global images, and because a large proportion of live cells are labeled, the image resolution is determined by the spatiotemporal resolution of the imaging device, not the dexterity of the operator, as is the case for traditional electroanatomical mapping. Therefore, optical electrophysiology mapping has potential to significantly advance the field, simplify and reduce the cost of procedures, and improve access to care.

In an exemplary embodiment, voltage-sensitive dyes may be used, e.g., in conjunction with the imaging catheter 20 shown in FIGS. 1 and 2. Once the distal end 24 is introduced into a chamber 94 of the heart 90, the balloon 30 may be inflated and pressing against the endocardium 92 to displace blood, allowing visualization of the endocardial surface through the balloon 30, and sufficiently minimizing motion to allow further minimal correction by filtering and ratiometry. Alternatively, the catheter 20 may include one or more features (not shown) for achieving mechanical stabilization of imaging relative to tissue in the beating heart. For example, the balloon surface may be adapted to adhere or stick to the heart surface. Alternatively, the catheter 30 may include prongs, barbs, and/or other features (not shown) extending therefrom to contact the heart surface. Further alternatively, suction or vacuum may be used to adhere the distal end of the catheter to the surface of the heart being imaged.

Alternatively, or in addition, image processing, e.g., by a controller (not shown), may be applied to achieve image stabilization in order to accurately measure optical signals. For example, morphological features identifiable on the heart surface throughout the contraction cycle may be registered and/or utilized as fiducial markers and the image stabilized by software means using such features as fixed references. Further, additional techniques or indicators of absolute position may be used in an image stabilization algorithm. Further, images may be stitched together using similar techniques, e.g., in order to provide enhanced spatial perspective and/or spatial orientation to the user.

In the exemplary embodiment shown in FIG. 2, the catheter 20 may include a channel for a coherent fiber bundle for imaging, e.g., emission of fluorescence light, a channel for infusion fluid (e.g., saline), a guide wire lumen, a steering mechanism, and light guides optically coupled to the appropriate LED, an excitation filter (used when LED emission is not narrow enough), and the like. Light, e.g., from LED1 and LED2 shown in FIG. 2, may be include one or more excitation sources located at the proximal end of the catheter 20 outside the patient's body. At least two light sources may be used for motion correction by ratiometry, though the system is adaptable to more or less than two light sources.

Excitation of the dye and the resulting emission may then be collected via a distal lens (e.g., grin, conventional, etc.) and then guided through the catheter coherent fiber bundle. On the imaging side, the light emission may then be processed, e.g., by one or more of beam expanding, filtering, light guiding, using a dichroic, and/or capturing using a camera, such as a high speed EMCCD camera where it may be band-passed filtered appropriately on the emission side, and then focused on the imaging sensor of the camera. The LED excitation may be driven by the frame-exposure signal of the camera. So, during frame exposure one, LED1 is on, and during frame exposure two LED 2 is on, etc. This system may be driven by custom microcontroller software, and the LEDs may be switched in the microsecond domain. Thus, the camera may image using one LED at a time, and so by interpolation, two signals may be followed. The LED microcontrollers may be controlled by the computer through USB or other appropriate interface.

Optionally, a laser or other treatment element, may be coupled to this same system for ablation purposes, for example via the coherent fiber bundle. For example, a long wavelength 980 nm diode laser may be passed through two identical half-spherical lens with one half movable by a xyz motorized micromanipulator driven by custom computer software so that ablation may be guided into the same or a separate coherent fiber bundle in order to effect ablation of the observed tissue.

It should be noted that, using any of the systems and methods herein, tissue having had dye introduced to it endocardially, epicardially and/or via the vasculature may be imaged endocardially and/or epicardially.

Further, imaging of tissue to which dye has been delivered or applied may be performed using one or more minimally invasive devices as we have elsewhere described, including direct visualization catheters, endoscopes, and the like.

The devices and methods described above may be applicable to other clinical setting other that cardiac electrophysiology (e.g., agents other than fluorescent dyes, including drugs, imaging or diagnostic agents, etc. and tissues other than the heart), where it is desirable to deliver a generally high concentration of agent to a target tissue.

Additionally, it may be useful to delivery agents with improved localization to cardiac tissue using an epicardial approach. For example, an agent may be introduced into the pericardial spaces as described above. Alternatively, an agent may be introduced continuously into the pericardial space, e.g., by drip infusion using and pericardial catheter. Such an approach may be useful for introducing various cardiac agents, e.g., inotropes, anti-arrhythmics, and/or other agents so as to increase local activity and minimize systemic effects.

The devices and methods described herein, while described as generally separate approaches, may be combined to achieve additive effect.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for imaging tissue structures of a heart within a body, comprising:
   introducing a distal end of an imaging device into a chamber of the heart;
   introducing a distal end of a delivery device into a coronary artery or vein of the heart;
   at least partially obstructing flow of blood into the coronary artery or vein using an expandable member on the distal end of the delivery device;
   with the imaging device distal end within the chamber, delivering fluorescent dye via the delivery device distally beyond the expandable member into the coronary artery or vein with the expandable member at least partially obstructing flow of blood into the coronary artery or vein to minimize absorption of the dye by blood within the coronary artery or vein such that the dye is absorbed by cardiac tissue adjacent the chamber; and
   acquiring images of the cardiac tissue adjacent the chamber using the imaging device, the dye enhancing imaging cardiac electrical activity within the cardiac tissue.

2. The method of claim 1, wherein the dye comprises at least one of a voltage-sensitive fluorescent dye and a calcium-sensitive fluorescent dye.

3. The method of claim 1, wherein the dye is delivered using a dye carrier to resist the dye mixing within blood within the one or more body lumens.

4. The method of claim 3, wherein the dye carrier comprises one or more of dimethyl sulfoxide (DMSO), iodinated contrast, and a biocompatible hydrogel.

5. The method of claim 1, wherein the dye is delivered within a micelle.

6. The method of claim 1, wherein the dye comprises protein molecules that temporarily reduce absorption of the dye by blood cells to enhance transit of the dye to capillaries of the cardiac tissue.

7. The method of claim 1, wherein the coronary artery or vein comprises a coronary artery.

8. The method of claim 1, wherein the delivery device comprises a catheter, and wherein the dye is delivered through a lumen of the catheter from the catheter distal end distally beyond the expandable member into the coronary artery or vein while the coronary artery or vein is at least partially obstructed.

9. The method of claim 8, wherein the catheter distal end is introduced into a coronary artery of the body and the expandable member is expanded to substantially seal the coronary artery, and where the dye is delivered from the catheter distal end into the coronary artery.

10. The method of claim 8, wherein the catheter distal end is introduced into the coronary sinus and the expandable member is expanded to substantially seal the coronary sinus, and wherein the dye is delivered from the catheter distal end retrograde into blood vessels communicating with the coronary sinus.

11. The method of claim 9, further comprising:
    introducing a distal end of a detection catheter into a coronary sinus of the body; and
    monitoring fluid flowing into the coronary sinus to identify dye within the fluid.

12. The method of claim 1, wherein the acquired images are used to identify one or more regions of the cardiac tissue for treatment, the method further comprising delivering energy to the one or more regions.

13. The method of claim 12, wherein delivering energy comprises delivering laser energy via the imaging catheter to ablate the one or more regions.

14. The method of claim 1, further comprising delivering a protective fluid via the delivery device into the coronary artery or vein simultaneously with delivering the dye to reduce mixing of the dye with blood and enhance transit of the dye to capillaries of the cardiac tissue.

15. A method for performing a procedure within of a heart of a body, comprising:
   introducing a distal end of an imaging catheter into a chamber of the heart;
   introducing a distal end of a delivery sheath different than the imaging catheter into a coronary artery or vein of the heart;
   at least partially obstructing flow of blood into the coronary artery or vein using an expandable member on the distal end of the delivery sheath;
   with the distal end of the imaging catheter in the chamber of the heart, delivering fluorescent dye distally beyond the expandable member into the coronary artery or vein from the delivery sheath with the expandable member at least partially obstructing flow of blood into the coronary artery or vein to minimize absorption of the dye by blood within the coronary artery or vein such that the dye is absorbed by cardiac tissue adjacent the chamber;
   acquiring images of the cardiac tissue adjacent the chamber using the imaging catheter, the dye identifying cardiac electrical activity within the cardiac tissue in the images; and
   ablating one or more regions of the cardiac tissue via the imaging catheter to modify the cardiac electrical activity.

16. The method of claim 15, further comprising acquiring additional images after ablating the one or more regions to confirm whether the cardiac electrical activity has been sufficiently modified.

17. The method of claim 16, further comprising further ablating the one or more regions after acquiring the additional images to further modify the cardiac electrical activity of the one or more regions.

18. The method of claim 15, wherein fluorescent dye is delivered into the coronary artery or vein from the delivery sheath with the imaging device distal end within the chamber.

19. The method of claim 15, wherein images of the cardiac tissue are acquired by an imaging element carried by the imaging catheter, and wherein ablating one or more regions of the cardiac tissue comprises delivering light via the imaging element to ablate the one or more regions.

20. A method for imaging tissue structures of a heart within a body, comprising:
   introducing a distal end of an imaging device into a chamber of the heart;
   introducing a delivery device into a coronary artery or vein of the heart;
   with the imaging device distal end within the chamber, delivering fluorescent dye via the delivery device into the coronary artery or vein such that the dye is absorbed by cardiac tissue adjacent the chamber; and
   acquiring images of the cardiac tissue adjacent the chamber using the imaging device, the dye enhancing imaging cardiac electrical activity within the cardiac tissue,
   wherein the dye is delivered in a protective configuration that reduces absorption of the dye by blood cells and enhances transit of the dye to capillaries of the cardiac tissue.

21. The method of claim 20, wherein the protective configuration comprises delivering the dye carried by a dye carrier that breaks down when passing from the coronary artery or vein into capillaries to enhance absorption of the dye by the cardiac tissue.

22. The method of claim 20, further comprising delivering a protective fluid via the delivery device into the coronary artery or vein simultaneously with delivering the dye to reduce mixing of the dye with blood and enhance transit of the dye to capillaries of the cardiac tissue.

* * * * *